United States Patent
Dipple et al.

(10) Patent No.: US 12,429,468 B2
(45) Date of Patent: Sep. 30, 2025

(54) SPATIALLY VARIED PLASMONIC-PHOTONIC SENSOR FOR DETECTION AND IDENTIFICATION OF AIRBORNE AGENTS

(71) Applicant: US Gov't as represented by Sec'y of Air Force, Wright-Patterson AFB, OH (US)

(72) Inventors: Kathleen Dipple, Destin, FL (US); Jimmy E. Touma, Shalimar, FL (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 861 days.

(21) Appl. No.: 17/687,777

(22) Filed: Mar. 7, 2022

(65) Prior Publication Data
US 2022/0291183 A1   Sep. 15, 2022

Related U.S. Application Data (60) Provisional application No. 63/159,705, filed on Mar. 11, 2021.

(51) Int. Cl.
*G01N 33/00* (2006.01)
*B82Y 15/00* (2011.01)
*B82Y 20/00* (2011.01)

(52) U.S. Cl.
CPC ..... *G01N 33/0001* (2013.01); *G01N 33/0062* (2013.01); *B82Y 15/00* (2013.01); *B82Y 20/00* (2013.01)

(58) Field of Classification Search
CPC ........... G01N 33/0001; G01N 33/0062; B82Y 15/00; B82Y 20/00
(Continued)

(56) References Cited

U.S. PATENT DOCUMENTS

| | | | | |
|---|---|---|---|---|
| 8,322,658 B2 * | 12/2012 | Gershzohn | ............. | G08B 17/00 244/129.2 |
| 8,717,558 B2 * | 5/2014 | Gu | ........................ | G01N 21/658 356/301 |

(Continued)

OTHER PUBLICATIONS

Potyrailo et al., "Discovery of the surface polarity gradient on iridescent Morpho butterfly scales reveals a mechanism of their selective vapor response," PNAS, vol. 110 (2013) 15567-15572.

(Continued)

*Primary Examiner* — Joshua E Rodden
(74) *Attorney, Agent, or Firm* — AFMCLO/JAZ; Eugene P. Sunday (57) ABSTRACT

An odor-localizing autonomous air vehicle includes an airborne robotic platform having a navigation platform, a wireless transmitter communicatively coupled to a management console, and an olfactory sensor mounted on the airborne robotic platform that reacts to at least one olfactory odor. A controller is communicatively coupled to the airborne robotic platform, the navigation platform, and the biological sensor. The controller monitors the olfactory sensor. In response to the biological sensor detecting the at least one olfactory odor, the controller directs the airborne platform to three-dimensionally map an olfactory plume of the at least one olfactory odor using an olfactory-driven search pattern. The controller stores the three-dimensional map for later retrieval or transmits the three-dimensional map of the olfactory plume to the management console via the wireless transmitter. The olfactory sensor is a photonic crystal enclosure that contains plasmonic nanoparticles.

2 Claims, 4 Drawing Sheets
(2 of 4 Drawing Sheet(s) Filed in Color)

(58) Field of Classification Search
USPC .......................................................... 244/1 R
See application file for complete search history.

(56) References Cited

U.S. PATENT DOCUMENTS

| | | | | |
|---|---|---|---|---|
| 9,797,060 | B2* | 10/2017 | Du ........................ | C25D 11/045 |
| 9,995,847 | B2* | 6/2018 | Kalagnanam ........... | G01W 1/10 |
| 10,712,280 | B2* | 7/2020 | Ge ........................ | G01N 21/658 |
| 11,959,859 | B2* | 4/2024 | Carlen ...................... | G01J 3/44 |
| 12,135,286 | B1* | 11/2024 | Mazed ................. | G06Q 20/321 |
| 2007/0020144 | A1* | 1/2007 | Du ......................... | B82Y 30/00 |
| | | | | 422/400 |
| 2010/0198521 | A1* | 8/2010 | Haick ..................... | B82Y 15/00 |
| | | | | 706/14 |
| 2015/0332523 | A1* | 11/2015 | Ranasinghe ......... | G06F 18/2433 |
| | | | | 701/34.2 |
| 2016/0363339 | A1* | 12/2016 | Blackley ................... | A61L 9/14 |
| 2017/0115218 | A1* | 4/2017 | Huang .................... | B60R 11/04 |
| 2017/0255198 | A1* | 9/2017 | Rodriguez ............ | G05D 1/0274 |
| 2017/0369168 | A1* | 12/2017 | Hwang .............. | G01N 33/0034 |
| 2019/0369595 | A1* | 12/2019 | Fievez ...................... | G01H 3/00 |
| 2020/0371530 | A1* | 11/2020 | Anderson ............ | G05D 1/0274 |
| 2022/0291183 | A1* | 9/2022 | Dipple ............... | G01N 33/0001 |
| 2023/0266291 | A1* | 8/2023 | Myrick ................ | G01N 21/658 |
| 2025/0014345 | A1* | 1/2025 | Kurfirst ................ | G06Q 30/018 |
| 2025/0035581 | A1* | 1/2025 | Akinwande ........ | G01N 27/4145 |

OTHER PUBLICATIONS

Potylrailo, "Multivariable sensors for ubiquitous monitoring of gases in the era of internet of things and industrial internet," Chem. Rev. vol. 116 (2016) 11877-11923.

Feng et al., "A Colorimetric Sensor Array for Identification of Toxic Gases below Permissible Exposure Limits," Suppl. Mater. for Chem. Comm., vol. 46 (2010) 18 pages total.

Feng et al., "A Colorimetric Sensor Array for Identification of Toxic Gases below Permissible Exposure Limits," Chem. Comm, vol. 46 (2010) 2037-2039.

Islam et al., "A Hi-Bi Ultra-Sensitive Surface Plasmon Resonance Fiber Sensor," IEEE Access, vol. 4 (2016) 11 pages total.

Xavier et al., "Advances in optoplasmonic sensors—combining optical nano/microcavities and photonic crystals with plasmonic nanostructures and nanoparticles," Nanophotonics, vol. 7 (2018) 1-38.

Liu et al., "Bio-Inspired Plasmonic Photocatalysts," Small Methods, vol. 3 (2019) 1800295 (14 pages total).

Kangas et al., "Colorimetric Sensor Arrays for hte Detection and Identification of Chemical Weapons and Explosives," Anal. Chem., vol. 47 (2017) 138-153.

Potyrailo et al., "Detection of Individual Vapors and Their Mixtures Using a Selectivity-Tunable Three-Dimensional Network of Plasmonic Nanoparticles," Angew. Comm. Int. Ed., vol. 52 (2013) 10360-10364.

Yue et al., "Gold nanoparticles as sensors in the colorimetric and fluorescence detection of chemical warfare agents," Coord. Chem. Rev., vol. 311 (2016) 75-84.

Kou et al., "High-sensitivie and stable photonic crystal sensors for visual detection and discrimination of volatile aromatic hydrocarbon vapors," Chem. Eng. J., vol. 375 (2019) 121987, 10 pages total.

Xie et al., "Imparting sensitivity and selectivity to a gold nanoparticle chemiresistor through thiol monolayer functionalization for sensing acetone," RSC Adv., vol. 8 (2018) 35618-35624.

Sen et al., "Low-cost colorimetric sensor for the quanititative detection of gaseous hydrogen sulfide," Sens. Act. B., vol. 134 (2008) 234-237.

Zhang et al., "Nanostructured material for room-temperature gas sensors," Adv. Mater., vol. 28 (2016) 795-831.

Wang et al., "The rich photonic world of plasmonic nanoparticle arrays," Mater. Today, vol. 21 (2018) 303-314.

Welearegay et al., "Ultrapure organically modified gold nanoparticles for breath analysis," Proc. Eng., vol. 168 (2016) 133-136.

* cited by examiner

SPATIALLY VARIED PLASMONIC-PHOTONIC SENSOR FOR DETECTION AND IDENTIFICATION OF AIRBORNE AGENTS

CROSS-REFERENCE TO RELATED APPLICATIONS

This application claims the benefit of priority under 35 U.S.C. § 119(e) to U.S. Provisional Application Ser. No. 63/159,705 entitled "Spatially Varied Plasmonic-Photonic Sensor for Detection and Identification of Airborne Agents", filed 11 Mar. 2021, the contents of which are incorporated herein by reference in their entirety.

ORIGIN OF THE INVENTION

This invention was made with government support under Contract No. FA9550-19-F-0007 between Air Force Office of Scientific Research and the National Academy of Sciences and assigned to United States Government and may be manufactured and used by or for the Government of the United States of America for governmental purposes without the payment of any royalties thereon or therefore.

BACKGROUND

1. Technical Field

The present disclosure generally relates to autonomous vehicles having sensors that detect characteristics of the air, and more particularly to autonomous airborne vehicles having olfactory sensing.

2. Description of the Related Art

Robotic airborne chemical source localization has critical applications ranging from search and rescue to hazard detection of pollution assessment. Previous demonstrations on flying robots have required search times in excess of ten minutes, or required computation intensive signal processing, largely because slow response of semiconductor gas sensors. Generally known systems for mapping and tracking an odor plume using an olfactory sensor require detection of the prevailing airflow using heavy sensors or a comparison between global positioning system (GPS) speed and visual ground track. The former prevents use of convenient, lightweight platforms and the latter prevents use indoors or in the presence of a GPS spoofer or jammer. Generally-known olfactory sensors are too slow for airborne sensing, especially three-dimensional mapping of an olfactory plume that rapidly changes with time.

SUMMARY

The present innovation overcomes the foregoing problems and other shortcomings, drawbacks, and challenges of mapping olfactory plumes. While the present innovation will be described in connection with certain embodiments, it will be understood that the invention is not limited to these embodiments. To the contrary, this invention includes all alternatives, modifications, and equivalents as may be included within the spirit and scope of the present invention.

According to one aspect of the present disclosure, a bio-hybrid odor-localizing autonomous air vehicle ("smellicoper") includes an airborne robotic platform. The smellicopter includes a navigation platform coupled to the airborne robotic platform. The smellicopter includes a biological sensor mounted on the airborne robotic platform that reacts to at least one olfactory odor. A controller of the smellicopter is communicatively coupled to the airborne robotic platform, the navigation platform, and the biological sensor. The controller monitors the biological sensor. In response to the biological sensor detecting the at least one olfactory odor, the controller directs the airborne platform to map an olfactory plume of the at least one olfactory odor using an olfactory-driven search pattern. In particular embodiments, the biological sensor is a spatially varied plasmonic-photonic sensor for detection and identification of airborne agents.

According to another aspect of the present disclosure, a bio-hybrid odor-localizing autonomous air vehicle (smellicopter) includes an airborne robotic platform comprising a drone copter. The smellicopter includes a navigation platform coupled to the airborne robotic platform. The smellicopter includes a wireless transmitter communicatively coupled to a management console. The smellicopter includes a memory containing an olfactory-driven search pattern. A biological sensor is mounted on the airborne robotic platform. The biological sensor reacts to at least one olfactory odor. A controller is communicatively coupled to the airborne robotic platform, the navigation platform, the wireless transmitter, the memory, and the biological sensor. The controller monitors the biological sensor. In response to the biological sensor detecting the at least one olfactory odor, the controller directs the airborne platform to map an olfactory plume of the at least one olfactory odor using an olfactory-driven search pattern. The controller associates detection of the olfactory plume with a location based on the navigation platform. The controller stores data of the mapping of the olfactory plume in the memory. The controller transmits a completed map to the management console using the wireless transmitter.

According to an additional aspect of the present disclosure, a method includes monitoring a biological sensor that reacts to at least one olfactory odor mounted on an airborne robotic platform of a bio-hybrid odor-localizing autonomous air vehicle. In response to the biological sensor detecting the at least one olfactory odor, the method includes directing the airborne platform to map an olfactory plume of the at least one olfactory odor using an olfactory-driven search pattern. The method includes associating detection of the olfactory plume with a location based on a navigation platform mounted on the airborne robotic platform. The method includes storing data of the mapping of the olfactory plume in a memory.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

According to aspects of the present innovation, the disclosure of commonly-owned and pending U.S. patent application Ser. No. 16/879,296 to Melanie Anderson et. al., entitled "A Bio-Hybrid Odor-Guided Autonomous Palm-Sized Air Vehicle", filed on 20 May 2020 (hereafter "Anderson application") is hereby improved with a novel plasmonic/photonic sensor. The Anderson application claims priority under 35 U.S.C. § 119(e) to U.S. Provisional Application Ser. No. 62/851,021, filed 21 May 2019, and Ser. No. 63/023,992, filed 13 May 2020, the contents of all three of which, including references cited therein, are incorporated herein by reference in their entirety.

Introduction and Purpose: Warfighters and first responders encounter great danger in the event of detecting an airborne chemical or biological agent in theater or during a disaster. Current detection methods require them to walk into potentially dangerous areas with bulky, handheld devices robed in cumbersome protective wear. The purpose of this invention is to relieve them of these precarious tasks by inventing a low cost, low power, low weight, and highly sensitive hybrid gas sensor.

Current state-of-the-art UAV and hand-held detectors are PID (particle ionization detectors), where a high energy source ionizes the airborne agents and the resulting electron is used to produce a signature signal. The issues with PIDs are that they require high power, large platforms, and can only detect very small (<10) different chemicals agents, and limited to one agent at a time.

Figure 4A:
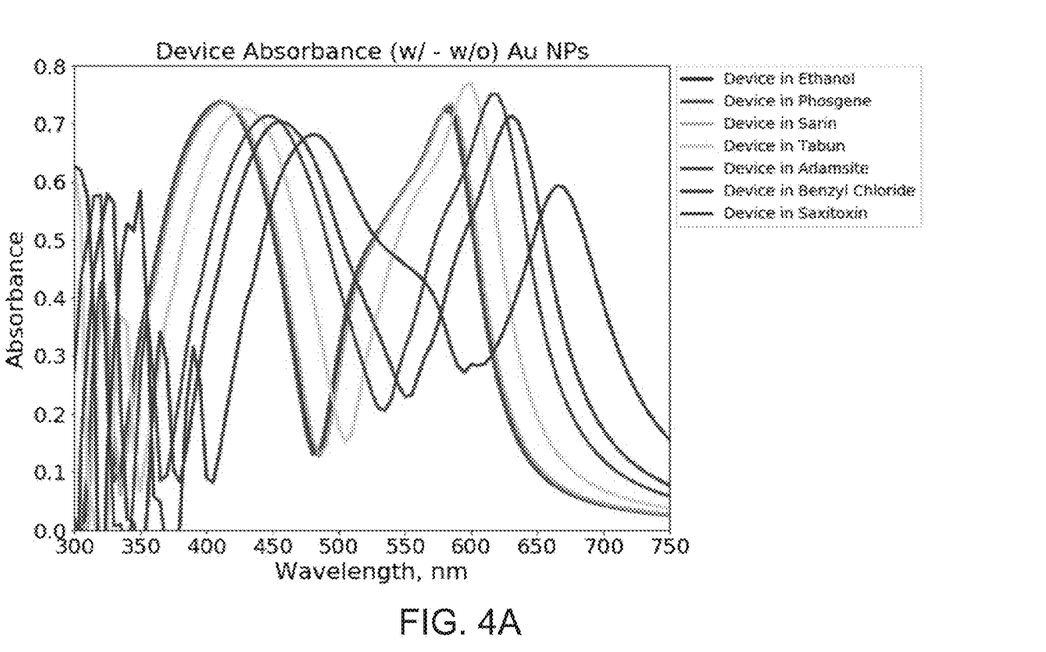
FIG. 4A is a graphical diagram of absorbance spectra of the PhC cell sensor, according to one or more embodiments.
Figure 4B:
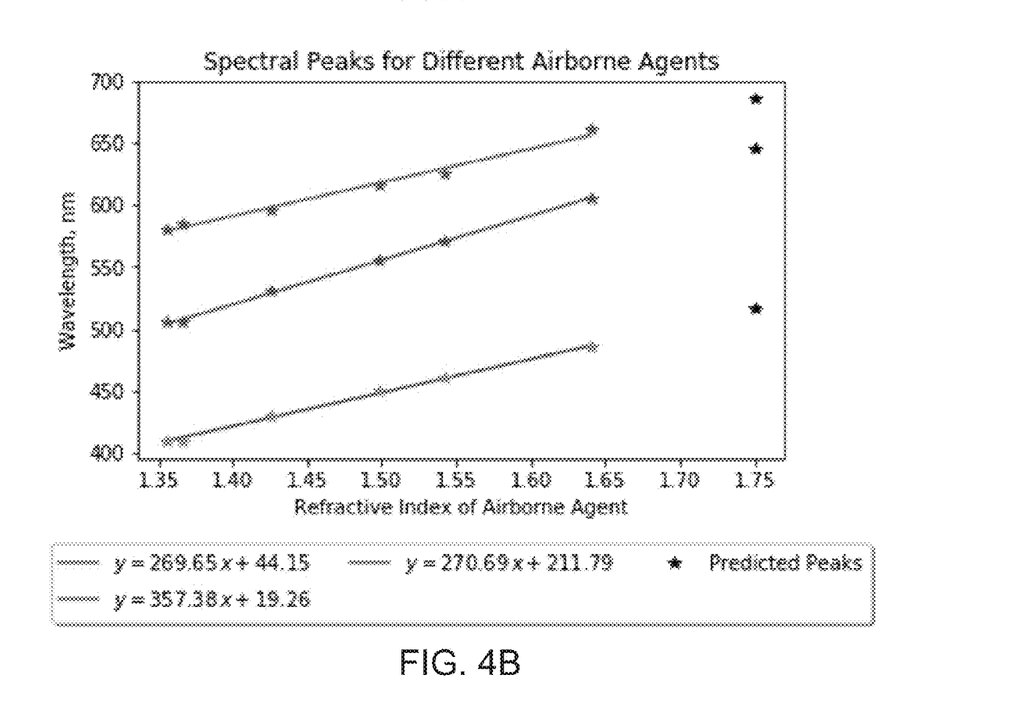
FIG. 4B is a graphical diagram of spectral dependence on refractive index of the PhC cell sensor, according to one or more embodiments.

Conversely, our sensor has a unique design and functionality to provide the necessary tools for the warfighters accomplish their mission without putting them in harm's way. The innovative aspects of our invention are as follows: (a) Reusable: the sensor is self-cleaning and can be used multiple times before disposal; (b) Reconfigurable: Change the intended use by changing the nanoparticle ligands and/or the PhC structure to target specific agents; (c) Multivariable sensing: can detect several agents at the same time; (d) Bio-inspired spatially varying lattice structure: provides polarity gradient with plasmonic nanoparticles incorporated into the structure; and (e) Identification of unknown gas based on color (index of refraction) using historical color profiles. See FIGS. 4A-4B.

The sensor may be used in different applications such as, but not limited to (i) home gases detection; (ii) food safety; (iii) medical diagnostics; (iv) pilot fatigue and dehydration; and (v) air quality.

Figure 1A:
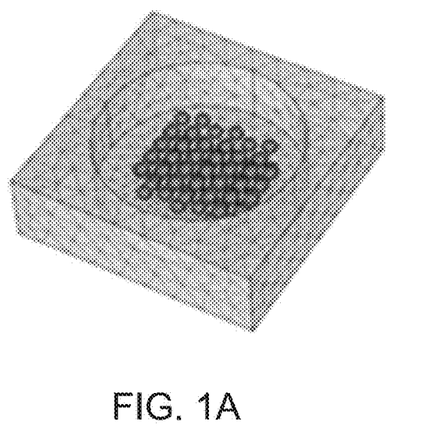
FIG. 1A depicts a three-dimensional mesh schematic of a photonic crystal (PhC) unit cell sensor filled with plasmonic nanoparticles, according to one or more embodiments.
Figure 1B:
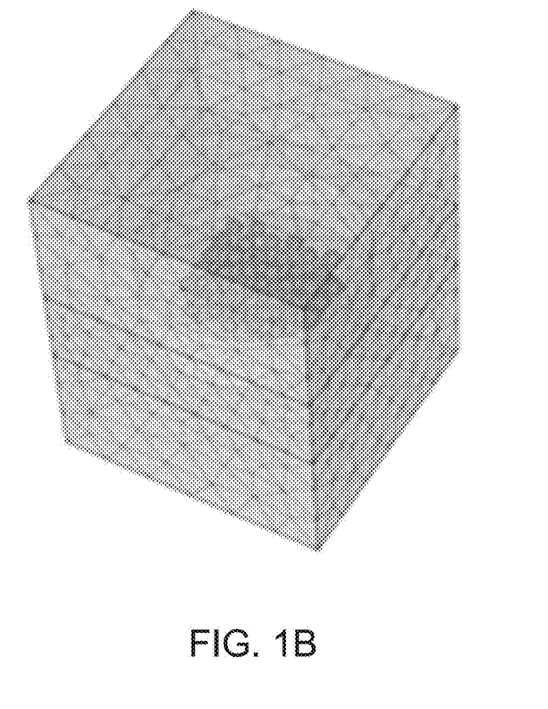
FIG. 1B depicts a three-dimensional mesh schematic of the PhC unit cell sensor of FIG. 1A in a cube filled with test airborne agent, according to one or more embodiments.

FIGS. 1A-1B are mesh versions of our sensor. FIG. 1A shows a photonic crystal unit cell filled with plasmonic nanoparticles. FIG. 1B shows the same well in a cube filled with a test airborne agent. Both situations were initially simulated using COMSOL Multiphysics software to obtain the optical characteristics of the device.

Description and Design of the Invention: The design of our sensor uses the basic properties of plasmonic nanoparticles and photonic crystals. When a noble metal nanoparticle is irradiated with light, its surface electrons begin to oscillate coherently, generating a strong localized electromagnetic field. Also known as a surface plasmon resonance, this field is extremely sensitive to changes in its vicinity. Also known are the color changing characteristics of spatially varying photonic crystals and their sensitivity to changes in the index of refraction of one of its constituent materials. Our invention combines these two effects to generate a novel, multivariable hybrid sensor. Our device consists of biologically inspired spatially-varying photonic crystal wells filled with plasmonic nanoparticles. We chose gold instead of the silver nanoparticles due of their high-sensitivity across the visible spectrum and robust nature and resistance to oxidation. The sensor has the ability to change color (reflectance) in different ways depending on the type and concentration of the airborne agent it makes contact with or is in its vicinity. Every aspect of the device's color-response has a strong correlation to the agent's refractive index. The color change is captured by a micro-camera that records the RGB color of the sensor and converts it to a reflectance profile in the visible spectrum, which is then compared with known spectra to identify the agent that caused the color change.

Making and Using the Innovation: Gold nanoparticles (approximately 5 nm diameter) were fabricated by the quick reduction of gold ions (from HAuCl4) by sodium borohydride in the presence of citrate ligands. Common (low refractive index material) photonic crystal structures are fabricated by multiphoton lithography. Plasmonic nanoparticles may be applied to a bio-inspired PhC by drop casting, or by spin coating (depending on the PhC). Excess NPs may be removed by + or wiping across with razor blade. The device is then placed in an enclosure that ensures uniform airflow over the sensor in one direction. A cellphone camera is placed above the sensor to record changes in color as air passes over the sensor. White LED lights, 101, are placed inside the enclosure to provide uniform illumination over the sensor but in locations that are not shining directly into the camera.

Figure 2:
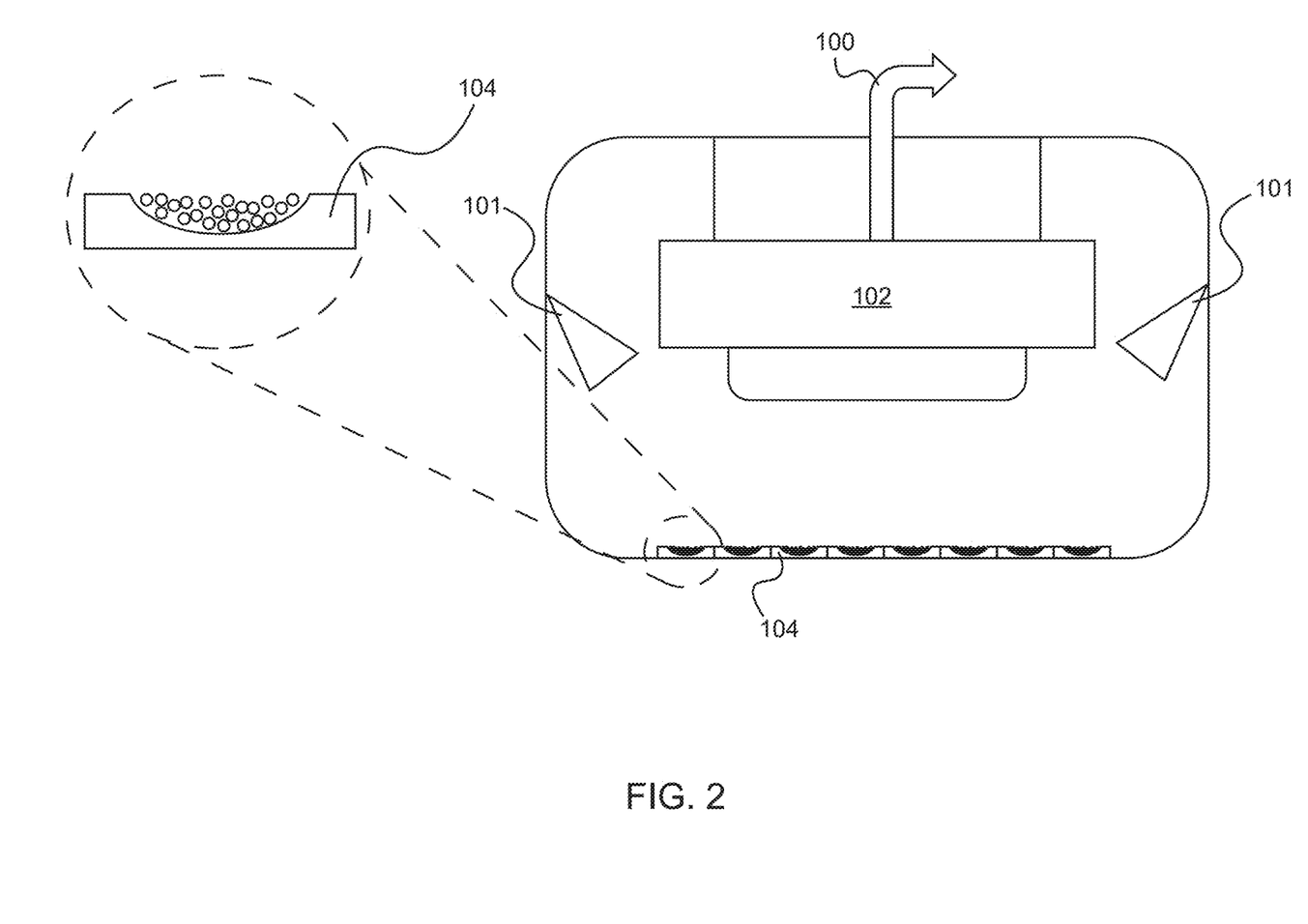
FIG. 2 depicts a cross sectional diagram of an enclosed sensor array, according to one or more embodiments.

FIG. 2 depicts a cross section of the enclosure with the sensor array, 104, at the bottom. The camera, 102, is fastened to the enclosure to prevent it from moving relative to the sensor, 104. A power and data cable, 100, is attached to the camera, 102 and exits the enclosure in an air-tight hole. Air is flowing uniformly orthogonal to the page.

Alternative Configuration and Usage: In the process of designing the sensor and identifying techniques on how to identify the change in the SPR due to the presence of an airborne agent, we identified two alternative configurations to measure this change in order to identify the said agent.

Figure 3A:
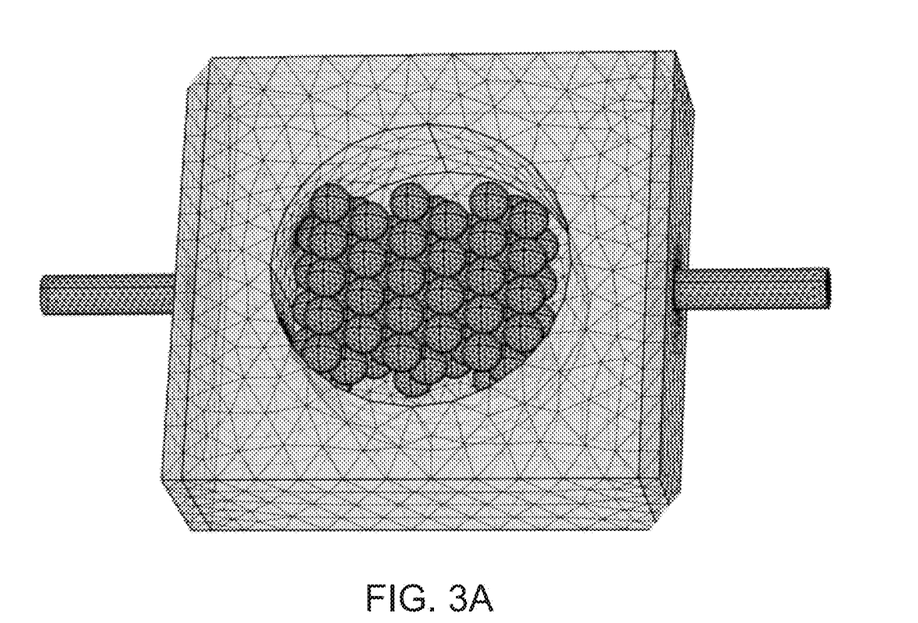
FIG. 3A depicts a three-dimensional mesh schematic of a PhC unit having a well between capacitor plates across the device, according to one or more embodiments.
Figure 3B:
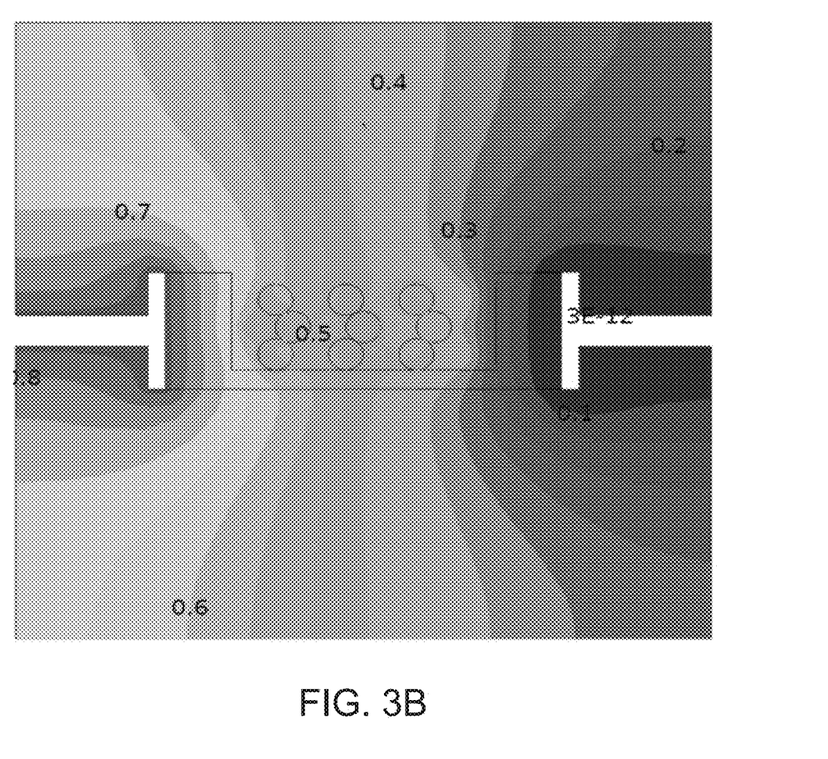
FIG. 3B depicts a graphical depiction of electrical potential between the capacitor plates of the PhC unit of FIG. 3A, according to one or more embodiments.

The first alternative configuration is to surround the well with a parallel-plate capacitor with a baseline potential difference. This is illustrated in FIG. 3a. When an agent attaches itself to the sensor or is in its vicinity, there would be a noticeable drop or change in the voltage that can be read out and measured. This change can then be correlated to previously tabulated changes for different agents and statistical likelihood of a particular agent can be computed and reported to the user. FIG. 3b shows a simulation of the baseline case without any external agent present.

FIG. 3A depicts a three-dimensional mesh schematic of a PhC unit having a well between capacitor plates across the device. FIG. 3B depicts a graphical depiction of electrical potential between the capacitor plates of the PhC unit of FIG. 3A.

The second alternative configuration, not illustrated in this draft, is to have a backplane readout of the transmitted light via optical fibers. Since the readout would record the intensity of the transmitted light instead of the reflected light, as described in the original design, the reconstruction of the spectrum would be opposite of the former design. This readout could done in such a way that the reconstruction of the transmitted spectrum is done in hardware which reduces the latency in identifying the agent that caused it.

Conclusion: presented above is the design, fabrication, and usage of airborne agent detection sensor. The different possible configurations of the sensor make it ideal for diverse set of applications. Moreover, we can use the dependence of the spectral peaks on the refractive index to extrapolate the refractive index of an unknown agent and identify it by comparing it to tabulated data.

FIG. 4A is a graphical diagram of absorbance spectra of the PhC cell sensor.

FIG. 4B is a graphical diagram of spectral dependence on refractive index of the PhC cell sensor.

The following references cited above are hereby incorporated by reference in their entirety:

[1]*Julia* M. Bingham, Jeffrey N. Anker, Lauren E. Kreno, and Richard P. Van Duyne. Gas Sensing with High-Resolution Localized Surface Plasmon Resonance Spectroscopy. JOURNAL OF THE AMERICAN CHEMICAL SOCIETY, 132(49):17358-17359, Dec. 15, 2010.

[2] Ying-Hao Chen, Wei-Hua Shi, Lin Feng, Xue-Ying Xu, and Ming-Yu Shang-Guan. Study on simultaneous sensing of gas concentration and temperature in one-dimensional photonic crystal. SUPERLATTICES AND MICROSTRUCTURES, 131:53-58, July 2019.

[3] Hong Chi, Zhen Xu, Xiaosen Duan, Jing Yang, Fuke Wang, and Zibiao Li. High-Performance Colorimetric Room-Temperature NO2 Sensing Using Spin-Coated Graphene/Polyelectrolyte Reflecting Film. ACS APPLIED MATERIALS & INTERFACES, 11(35): 32390-32397, SEP 4, 2019.

[4] Christian Driau, Cristian Fabrega, Ismael Benito-Altamirano, Peter Pfeiffer, Olga Casals, Hongqiang Li, and Joan Daniel Prades. How to implement a selective colorimetric gas sensor with off the shelf components? SENSORS AND ACTUATORS B-CHEMICAL, 293:41-44, Aug. 15, 2019.

[5] Oriol Gonzalez, Sergio Roso, Xavier Vilanova, and Eduard Llobet. Enhanced detection of nitrogen dioxide via combined heating and pulsed UV operation of indium oxide nano-octahedra. BEILSTEIN JOURNAL OF NANOTECHNOLOGY, 7:1507-1518, Oct. 25, 2016.

[6] Jiaqing He, Nicolo Simone Villa, Zhen Luo, Shun An, Qingchen Shen, Peng Tao, Chengyi Song, Jianbo Wu, Tao Deng, and Wen Shang. Integrating plasmonic nanostructures with natural photonic architectures in Pd-modified Morpho butterfly wings for sensitive hydrogen gas sensing. RSC ADVANCES, 8(57):32395-32400, 2018.

[7] Gisu Heo, Ramalingam Manivannan, Hyorim Kim, and Young-A Son. Liquid and gaseous state visual detection of chemical warfare agent mimic DCP by optical sensor. DYES AND PIGMENTS, 171, December 2019.

[8] Md. Saiful Islam, Cristiano M. B. Cordeiro, Jakeya Sultana, Rifat Ahmmed Aoni, Shilun Feng, Rajib Ahmed, Mohsen Dorraki, Alex Dinovitser, Brian Wai-Him Ng, and Derek Abbott. A Hi-Bi Ultra-Sensitive Surface Plasmon Resonance Fiber Sensor. IEEE ACCESS, 7:79085-79094, 2019.

[9] Md. Saiful Islam, Jakeya Sultana, Ahmmed. A. Rifat, Rajib Ahmed, Alex Dinovitser, Brian W. H. Ng, Heike Ebendorff-Heidepriem, and Derek Abbott. Dual-polarized highly sensitive plasmonic sensor in the visible to near-IR spectrum. OPTICS EXPRESS, 26(23):30347-30361, Nov. 12, 2018.

[10] Donghui Kou, Yongce Zhang, Shufen Zhang, Suli Wu, and Wei Ma. High-sensitive and stable photonic crystal sensors for visual detection and discrimination of volatile aromatic hydrocarbon vapors. CHEMICAL ENGINEERING JOURNAL, 375, Nov. 1, 2019.

[11] Ching-Fu Lin, Hsiao-Wen Zan, Chia-Jung Lu, Hsin-Fei Meng, and Olivier Soppera. A low-cost miniaturized colorimetric sensor with vertically-stacked semi-transparent finger-type organic photo detector for formaldehyde sensing. ORGANIC ELECTRONICS, 73:115-121, October 2019.

[12] Haleh Nazemi, Aashish Joseph, Jaewoo Park, and Arezoo Emadi. Advanced Micro- and Nano-Gas Sensor Technology: A Review. SENSORS, 19(6), Mar. 2, 2019.

[13] Dnyandeo Pawar and Sangeeta N. Kale. A review on nanomaterial-modified optical fiber sensors for gases, vapors and ions (vol 186, 253, 2019). MICROCHIMICA ACTA, 186(5), May 2019.

[14] Radislav A. Potyrailo. Multivariable Sensors for Ubiquitous Monitoring of Gases in the Era of Internet of Things and Industrial Internet (vol 116, pg 11877, 2016). CHEMICAL REVIEWS, 116(23):14918, Dec. 14, 2016.

[15] Radislav A. Potyrailo, Michael Larsen, and Orrie Riccobono. Detection of Individual Vapors and Their Mixtures Using a Selectivity-Tunable Three-Dimensional Network of Plasmonic Nanoparticles. ANGEWANDTE CHEMIE-INTERNATIONAL EDITION, 52(39):10360-10364, SEP 23, 2013.

[16] Meng Qin, Mo Sun, Ruobing Bai, Yiqi Mao, Xiaoshi Qian, Dipika Sikka, Yuan Zhao, Hang Jerry Qi, Zhigang Suo, and Ximin He. Bioinspired Hydrogel Interferometer for Adaptive Coloration and Chemical Sensing. ADVANCED MATERIALS, 30(21), May 24, 2018.

[17] Laifa Sang, Guogang Xu, Zhiwei Chen, Xinzhen Wang, Hongzhi Cui, Gaoyu Zhang, and Yajie Dou. Synthesis and characterization of Au-loaded SnO2 mesoporous spheres by spray drying and their gas sensing. MATERIALS SCIENCE IN SEMICONDUCTOR PROCESSING, 105, January 2020.

[18] Avijit Sen, Jeffrey D. Albarella, James R. Carey, Patrick Kim, and William B. McNamara, III. Low-cost colorimetric sensor for the quantitative detection of gaseous hydrogen sulfide. SENSORS AND ACTUATORS B-CHEMICAL, 134(1):234-237, Aug. 28, 2008.

[19] Marco Sturaro, Enrico Della Gaspera, Niccolo Michieli, Carlo Cantalini, Seyed Mahmoud Emamjomeh, Massimo Guglielmi, and Alessandro Martucci. Degenerately Doped Metal Oxide Nanocrystals as Plasmonic and Chemoresistive Gas Sensors. ACS APPLIED MATERIALS & INTERFACES, 8(44):30440-30448, Nov. 9, 2016.

[20] Mahsa Vakili and Mina Noori. A Highly Accurate Refractive Index Sensor with Two Operation Modes Based on Photonic Crystal Ring Resonator. ANNALEN DER PHYSIK, 531(7), July 2019.

[21] Zhenzhen Xie, Mandapati V. Ramakrishnam Raju, Andrew C. Stewart, Michael H. Nantz, and Xiao-An Fu. Imparting sensitivity and selectivity to a gold nanoparticle chemiresistor through thiol monolayer functionalization for sensing acetone. RSC ADVANCES, 8(62):35618-35624, 2018.

[22] Guozong Yue, Song Su, Na Li, Maobing Shuai, Xinchun Lai, Didier Astruc, and Pengxiang Zhao. Gold nanoparticles as sensors in the colorimetric and fluorescence detection of chemical warfare agents. COORDINATION CHEMISTRY REVIEWS, 311:75-84, Mar. 15 2016.

[23] Jun Zhang, Xianghong Liu, Giovanni Neri, and Nicola Pinna. Nanostructured Materials for Room-Temperature Gas Sensors. ADVANCED MATERIALS, 28(5):795-831, Feb. 3, 2016.

[24] Zhonghai Zhang, Lianbin Zhang, Mohamed Nejib Hedhili, Hongnan Zhang, and Peng Wang. Plasmonic Gold Nanocrystals Coupled with Photonic Crystal Seamlessly on TiO2 Nanotube Photoelectrodes for Efficient Visible Light Photoelectrochemical Water Splitting. NANO LETTERS, 13(1):14-20, January 2013.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

In the preceding detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. It is also to be understood that other embodiments may be utilized and that logical, architectural, programmatic, mechanical, electrical and other changes may be made without departing from general scope of the disclosure. The following detailed description is, therefore, not to be taken in a limiting sense, and the scope of the present disclosure is defined by the appended claims and equivalents thereof.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

It is understood that the use of specific component, device and/or parameter names and/or corresponding acronyms thereof, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that terms is utilized.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope of the disclosure. The described embodiments were chosen and described in order to best explain the principles of the disclosure and the practical application, and to enable others of ordinary skill in the art to understand the disclosure for various embodiments with various modifications as are suited to the particular use contemplated.

What is claimed is:

1. A bio-hybrid odor-localizing autonomous air vehicle comprising:
   an airborne robotic platform;
   a navigation platform coupled to the airborne robotic platform;
   an olfactory sensor mounted on the airborne robotic platform that reacts to at least one olfactory odor and comprises plasmonic nanoparticles within a photonic crystal enclosure;
   a controller communicatively coupled to the airborne robotic platform, the navigation platform, and the olfactory sensor, and which:
   monitors the olfactory sensor;
   in response to the olfactory sensor detecting the at least one olfactory odor, directs the airborne platform to map an olfactory plume of the at least one olfactory odor using an olfactory-driven search pattern,
   once the olfactory sensor detects the at least one olfactory odor, the controller directs the removal of the olfactory odor from the olfactory sensor allowing the olfactory sensor to detect at least one more compound.

2. The bio-hybrid odor-localizing autonomous air vehicle of claim 1 wherein the intended use can be altered by changing nanoparticle ligands and/or the photonic crystal structure within the olfactory sensor to target specific agents.

* * * * *